United States Patent [19]

Platz

[11] Patent Number: 5,504,267
[45] Date of Patent: Apr. 2, 1996

[54] RESOURCE RECOVERY BY CATALYTIC CONVERSION OF POLYMERS

[75] Inventor: Gerald M. Platz, Conroe, Tex.

[73] Assignee: S-P Reclamation, Inc., Houston, Tex.

[21] Appl. No.: 289,187

[22] Filed: Aug. 11, 1994

Related U.S. Application Data

[63] Continuation-in-part of Ser. No. 107,281, Aug. 16, 1993, Pat. No. 5,369,215, which is a continuation-in-part of Ser. No. 864,426, Apr. 6, 1992, Pat. No. 5,264,640.

[51] Int. Cl.$^6$ .............................. C07C 1/00; C07C 4/00; C10G 1/00; C10G 1/10
[52] U.S. Cl. .......................................... 585/241; 585/240
[58] Field of Search .............................................. 585/241

[56] References Cited

U.S. PATENT DOCUMENTS

| | | | |
|---|---|---|---|
| 3,424,822 | 1/1969 | Liston | 260/881 |
| 3,494,958 | 2/1970 | Mannsfeld et al. | 260/486 |
| 3,558,589 | 1/1971 | Bethea et al. | 260/94.7 |
| 3,582,279 | 5/1971 | Beckman et al. | 23/209.2 |
| 3,704,108 | 11/1972 | Alpert | 44/62 |
| 3,974,206 | 8/1976 | Tatsumi et al. | 260/486 |
| 3,978,199 | 8/1976 | Maruhnic et al. | 423/461 |
| 3,996,022 | 12/1976 | Larsen | 44/1 |
| 3,997,407 | 12/1976 | Fujii et al. | 202/221 |
| 4,025,990 | 5/1977 | Lovette, Jr. | 241/DIG. 37 |
| 4,029,550 | 6/1977 | Mitsui et al. | 201/2.5 |
| 4,030,984 | 6/1977 | Chambers | 201/25 |
| 4,045,370 | 8/1977 | Cares | 252/458 |
| 4,051,212 | 9/1977 | Grigat et al. | 264/DIG. 69 |
| 4,082,615 | 4/1978 | Komuro et al. | 201/12 |
| 4,098,649 | 7/1978 | Redker | 264/DIG. 69 |
| 4,108,730 | 8/1978 | Chen et al. | 201/2.5 |
| 4,175,211 | 11/1979 | Chen et al. | 585/241 |
| 4,240,587 | 12/1980 | Letsch | 241/DIG. 37 |
| 4,250,158 | 2/1981 | Solbakken et al. | 585/241 |
| 4,284,616 | 8/1981 | Solbakken et al. | 423/461 |

(List continued on next page.)

FOREIGN PATENT DOCUMENTS

| | | |
|---|---|---|
| 47-3017 | 8/1972 | Japan . |
| 47-30107 | 8/1972 | Japan .............................. 264/DIG. 69 |

OTHER PUBLICATIONS

"Thermocatalytic Degradation of Butyl Rubber in Presence of Combinations of AICl$_3$ With Some Metal Chlorides", S. R. Ivanova et al., Polymer Science U.S.S.R., pp. 265–272 (1983).

"Scrap Tires: A Resource and Technology Evaluation of Tire Pyrolysis and Other Selected Alternate Technologies," J. Dodds et al., prepared for the U.S. Department of Energy and Idaho National Engineering Laboratory, DE–AC07–76ID01570, Nov. 1983.

"Waste Tire Utilizaiton," R. L. Hershey et al., prepared for the U.S. Department of Energy, Office of Industrial Programs, AC01–84CE40714, Apr. 30, 1987.

(List continued on next page.)

Primary Examiner—Sharon Gibson
Attorney, Agent, or Firm—Arnold, White & Durkee

[57] ABSTRACT

A process is disclosed for the thermal catalytic conversion of polymeric feedstocks, such as scrap tire rubber or plastics, to recover valuable hydrocarbons for reuse. The process includes the solvent washing of -6 mesh polymer feedstock to remove the stabilizing additives which have migrated to the surface of the individual polymer particles. Prior to the reaction step the washed and dried polymer particulate are blended with a metallic halide catalyst system. The mixture of polymer particulate and catalyst are continuously fed to a reactor wherein the conversion of the polymer is accomplished. The reactor and downstream process units are continuously swept by an inert gas which is maintained at just above atmospheric pressure. The combination of the reactor temperature and pressure, with the catalyst system, cause a conversion of the polymer particles to valuable gaseous hydrocarbons. The inert gas, functioning as a sparger gas, sweep the gaseous hydrocarbons from the reactor to downstream separation equipment of conventional design wherein the gaseous products are recovered for future reuse. A carbon black residue is separately recovered for subsequent processing.

17 Claims, 5 Drawing Sheets

U.S. PATENT DOCUMENTS

| | | | |
|---|---|---|---|
| 4,402,791 | 7/1983 | Brewer | 585/241 |
| 4,426,459 | 1/1984 | Watabe et al. | 585/241 |
| 4,430,160 | 2/1984 | DuBow | 201/19 |
| 4,452,154 | 6/1984 | Kono et al. | 110/346 |
| 4,452,155 | 6/1984 | Ishihara et al. | 110/346 |
| 4,458,095 | 7/1984 | Wingfield, Jr. et al. | 585/241 |
| 4,507,174 | 3/1985 | Kutrieb | 585/241 |
| 4,515,659 | 5/1985 | Wingfield, Jr. et al. | 585/241 |
| 4,577,564 | 3/1986 | Tomita et al. | 110/110 |
| 4,579,871 | 4/1986 | Linden et al. | 521/43 |
| 4,588,477 | 5/1986 | Habib | 201/25 |
| 4,726,819 | 2/1988 | Michimae et al. | 55/20 |
| 4,740,270 | 4/1988 | Roy | 201/35 |
| 4,746,406 | 5/1988 | Timmann | 585/241 |
| 4,787,321 | 11/1988 | Schnellbacher et al. | 110/258 |
| 4,822,573 | 4/1989 | Timmann | 422/143 |
| 4,839,151 | 6/1989 | Apffel | 423/449 |
| 4,851,601 | 7/1989 | Fukuda et al. | 585/241 |
| 4,863,106 | 9/1989 | Perkel | 241/DIG. 37 |
| 4,871,426 | 10/1989 | Lechert et al. | 201/2.5 |
| 4,895,083 | 1/1990 | McDilda | 110/235 |
| 5,057,189 | 10/1991 | Apffel | 202/113 |
| 5,070,109 | 12/1991 | Ulick et al. | 521/41 |
| 5,084,141 | 1/1992 | Holland | 585/241 |
| 5,087,436 | 2/1992 | Roy | 423/461 |
| 5,162,446 | 11/1992 | Gibler | 525/338 |
| 5,216,149 | 6/1993 | Evans et al. | 540/538 |
| 5,230,777 | 7/1993 | Jarrell | 202/97 |
| 5,233,037 | 8/1993 | Nielinger et al. | 540/540 |
| 5,283,318 | 2/1994 | Saleh et al. | 528/481 |
| 5,286,374 | 2/1994 | Chen | 208/400 |
| 5,315,055 | 5/1994 | Butcher, Jr. | 585/241 |
| 5,321,174 | 6/1994 | Evans et al. | 585/241 |
| 5,326,919 | 7/1994 | Paisley et al. | 585/241 |

OTHER PUBLICATIONS

"Raw Material Recovery From Scrap Tires and Plastic Waste by Pyrolysis," W. Kaminsky et al., pp. 681–685.

"Recycling of Scrap Rubber as a Filler for Thermoplastics (Block, Sheet, Film) After a Controlled Pyrolysis and Crushing," by J. M. Vergnaud et al., pp. 187, 188.

"Pryolysis in a Fluidized Bed–A Recycling Process Developing Towards A Production Scale Plant," H. Timmann.

"Resource Recovery," C95/85, D. V. Jackson et al., 1985.

Kirk–Othmer Encyclopedia of Chemical Technology, 3rd Ed., vol. 19, pp. 1002–1010, 1982.

Thermodynamics of Polymerization, H. Swada, Dekker, 1976, pp. 2–5; 7–10; pp. 311–313; 318–325.

Macromolecules, Bovey and Winslow, Academic Press, 1979, pp. 431–433.

Encyclopedia of Polymer Science and Engineering, Wiley Interscience, vol. 4, pp. 719–744.

Polymer Handbook, Third Edition, J. Brandrup et al., Wiley Interscience, 1989, pp. II 275–290.

Rubber Chemistry and Technology, vol. 64, "The Ozonation of N,N'–DI–n–Octyl–p–Phenylenediamine and N,N'–DI–(1,1–Dimethylethyl)–p–Phenylenediamine", R. P. Lattimer et al., pp. 780–789.

"Recycling von Altreifen durch Pyrolyse in der Wirbelschicht," Prof. Dr. W. Kaminsky et al., pp. 181–196.

"Pyrolyse von Kunststoffabfällen (Recycling)," Kunststoffe–Plastics, pp. 20–24, Feb. 1986.

"Ein Verfahren zur Abfallbeseitigung und Rohstoffrückgewinnung," Dr. Bracker, Herne, pp. 46–48, Apr. 1981.

"Verarbeitung von Kunststoffmüll und Altreifen zu Chemie–Rohstoffen, besonders durch Pyrolyse," Prof. Dr. H. Sinn, et al. pp. 1–35.

Search 1–Report, InfoMaster (R) Service (c) 1990 Telebase Systems, Inc., U.S. Pat. No. 4,774,655, pp. 29–31, Jun. 6, 1990, Search Parameter: Tires and (Reclaim/or Recycl/) and Depolymer/.

Search 2–Report, Chemical Abstracts (1967–Present) via EasyLink, pp. 32–60, Jun . 7, 1990, Search Parameter: Tires and (Reclaim/ or Recycl/) and Pyroly/.

U.S. PTO Classification and Search Support Information System (1969 to Date), pp. 1–4, Mar. 23, 1992, (Conducted at Rice University), Search Parameter: Ozon* and (Depoly* or Degrad*).

U.S. PTO Classification and Search Support Information System, (1969–Date), pp. 1–21, Mar. 25, 1992, (Conducted at Rice University), Search Parameter: (Plastic or Poly* or Rubber or Tires) and Depoly*.

U.S. PTO Classification and Search Support Information System, (1969–Date), pp. 1–29, Mar. 25, 1992, (Conducted at Rice University), Search Parameter: (Plastic or Poly* or Rubber or Ties) and Ozone*.

U.S. PTO Classification and Search Support Infomation System (1969–Date), pp. 1–5, Mar. 25, 1992, (Conducted at Rice University), Search Parameter: (Recycl* or Reclam* or Reclaim*) and Ozon*.

"Pyrolysis of Polymers", Chapter 6, by Walter Kaminsky, 1992, pp. 60–72.

RESOURCE RECOVERY BY CATALYTIC CONVERSION OF POLYMERS

This patent application claims the benefit of and is a continuation-in-part of U.S. application Ser. No. 08/107,281, filed Aug. 16, 1993, now U.S. Pat. No. 5,369,215, entitled "Depolymerization Method for Resource Recovery From Polymeric Wastes," which claims the benefit of and is a continuation-in-part of prior filed U.S. application Ser. No. 07/864,426, filed Apr. 6, 1992, now U.S. Pat. No. 5,264,640.

BACKGROUND OF THE INVENTION

1. Field of Invention

The present invention relates to a thermocatalytic conversion process for recovering the original monomers, and/or other valuable hydrocarbons and solid residues, such as carbon black, from which polymerized products such as scrap or wastes tires, scrap rubber, and plastics can be created. Although reference is made in this application primarily to scrap tires and the hydrocarbons recovered therefrom, it should be recognized that a number of different polymerized products can substitute for scrap tires and that from such products a number of products and resources such as valuable hydrocarbons and solid products can be recovered.

Each year approximately 240 million used tires are discarded in the United States. Similar amounts are also annually discarded in other countries of the world. Likewise very large tonnages of plastic waste, a small amount of which is recovered for recycling, finds its way via disposal of household garbage, into landfill space. This combined tonnage of waste rubber tires and plastic waste strongly indicates that a near desperate need exists for a process that can economically recover for reuse the hydrocarbons from which commercial plastics and scrap rubber tires are made. Hence, a considerable amount of attention has been and continues to be devoted by industry and government agencies to various methods of utilizing waste scrap tires.

Some research and commercial efforts have been directed toward the development of new uses for old tires. Unprocessed used tires have been used in playgrounds, flower planters, and shoe soles, and tire pieces have been used as gaskets, shims, dock bumpers, and shock absorbers. The use of processed used tires in road construction is also gaining some attention. Paving materials made from a combination of crumb rubber and asphalt may last up to three times as long as standard paving materials. However, because of the high costs associated with the use of scrap tires for roads, this approach has not gained wide acceptance. Studies continue to explore this use of scrap tires in addition to the somewhat more conventional use of tires as crash barriers and impact absorbers around highway and bridge abutments. However, these new uses for used fires only consume a minor portion of the annual accumulation of scrap tires.

Consequently, significant research and commercial activity has been directed toward development of the use of scrap tires as an energy source. The 240 million used tires discarded each year represent upwards of $7 \times 10^{13}$ BTU's of energy. Two approaches to tapping this energy source have received most of the attention. In the first, either whole or shredded tires alone are burned for fuel in incinerators or specially designed boilers, in many cases to generate electricity, or are added directly to cement kilns. In many tire incinerators combustion is not complete, resulting in the discharge of smoke and objectionable odors. Meeting federal emissions regulations for any combustion system is costly. In the second approach, tires have the steel belts removed by extensive shredding and are then combined with wood, paper pulp, or other refuse to get a fuel blend that can be burned to provide energy. While the combination of tires with other materials results in a higher total average BTU content for burning as compared to the other materials alone, difficulty in handling, which typically includes special feeding and blending equipment, makes this second approach a rather unattractive method for reclaiming scrap tires. Moreover, for some the incineration of waste plastics has been used to recover their BTU value, identical to the use of scrap tires as fuel.

While such approaches might seem attractive given rising natural-gas and fuel-oil costs, one major drawback to the approach is that valuable basic chemical building blocks or monomers, such as styrene, instead of being recovered, are consumed. The cost of these destroyed or lost monomers includes the costs, in energy and finite natural hydrocarbon resources, of exploration and drilling for new oil and the costs of transporting the crude oil and converting it to the intermediate chemicals from which rubber is made. Ethylene, propylene, butadiene, and styrene are a few examples of monomers derived from petrochemical sources and used in tire manufacture. The total energy required to make the monomers in the tires is on the order of 60,000 BTU per lb. The fuel energy value of a tire is approximately 15,000 BTU per lb. The cost to the environment of using the valuable monomers as fuel, rather than reclaiming and recycling them, would include the costs of the energy and finite natural resources used to make them, which are permanently lost, versus the relatively meager amount of energy and no natural resources recovered when they consumed. In addition, the costs to the environment of replacing rather than reclaiming the monomers includes the burden of the additional carbon dioxide generated by the energy used in replacement. Carbon dioxide, according to many studies, contributes to global warming. Thus, given the drawback associated with these uses for scrap tires, there has been a search for alternative uses for scrap tires that are less costly and that have minimal adverse impact on the environment.

Tires generally consist of rubber, carbon black, steel, fabric, and other additives. Styrene-butadiene rubber is most commonly used in tire manufacturing, usually in combination with other elastomers such as natural rubber and ethylene propylene diene monomer (EPDM). Carbon black is used in the manufacture of tires to strengthen the rubber and increase resistance to abrasion. Steel, fiberglass, or fabric in the form of cords or belts is also present for reinforcement in the majority of tires produced today. Finally, other additives, such as antioxidants and antiozonants, are used in the tire manufacturing process to inhibit rubber deterioration and slow aging.

Polymerization is the process in which individual monomers join together in large numbers to form a polymer molecule. Where two different monomers join to form a polymer chain, a copolymer is produced. There are two broad classes or polymers and copolymers based on their polymerization: condensation polymers, such as polyesters, nylon, polycarbonates, and polyurethanes, are those whose polymerized form has a lower molecular weight than the sum of the monomers used to make it (the balance is generated as other chemicals such as methanol or glycols during polymerization). Addition, or chain-growth, polymers, such as polyethylene and polypropylene, are those whose polymerized form has the same molecular weight as the sum of the monomers used to make them. Addition or chain-growth, polymers are made in specific conditions of temperature and pressure and in the presence of an initiator (a form of catalyst) in which the polymer chain is propagated, or "zipped" together. Styrenebutadiene rubber, EPDM, and natural rubber, which are the polymers used in tire manufacture, are additive polymers.

There are basically two ways to break down a polymer: pyrolysis and depolymerization. Pyrolysis, also known as thermal cracking, is a process in which polymer molecules are heated until they fragment into several smaller, dissimilar, random-sized molecules. Pyrolysis typically results in the polymer molecules breaking down into a complex mixture of alcohols, hydrocarbons, and other molecules, none of which is an original monomer. Overall, the thermal conditions required for depolymerization are significantly milder than those associated with pyrolysis processes.

Depolymerization, the second way to break down a polymer, is essentially the opposite of polymerization. In the depolymerization of condensation polymers, prior art teaches several hydrolytic methods, such as glycolysis, methanolysis, or hydrolysis, categorized by the depolymerization reactant used, such as glycol, methanol or water, respectively, wherein, under specific conditions of temperature and pressure and sometimes, in the present of a catalyst, the reactant is added to the polymer causing the polymer chain to separate into its original monomers. An example of these methods is the recycling of PET (polyethylene terephthalate) bottles by a methanolysis process which produces the raw material DMT (dimethyl terephthalate, a precursor to PET, and ethylene glycol. The DMT is then blended with virgin feedstock and FDA-acceptable polymers for food bottles are made. Hydrolytic depolymerization methods have not proven to be effective with addition polymers.

2. The Prior Art

While not limited solely to additive, or chain-growth, polymers, the present invention teaches a method for their depolymerization. The process specifically creates conditions of temperature and pressure and the presence of a catalyst to depropagate or depolymerize these polymers to their constituent monomers. The depolymerization temperature and pressure ranges for many types of polymers and copolymers of the monomers from which the tires are made are well documented in the technical literature. The thermodynamics for the depolymerization of polymers is elucidated in "Thermodynamics of Polymerization" by H. Sawada, published by M. Dekker, 1976. As explained by Sawada, each polymer will have different conditions for depolymerization. For example, polybutadiene depolymerizes in the 325° C. to 475° C. range, while a 75/25 polybutadiene/styrene copolymer depolymerizes in the 327° C. range. Generally, the temperatures involved in the depolymerization of the polymers and copolymers from which tires are made are in the 135° C. to 500° C. range. However, neither the technical literature nor prior patents teach a process for the depolymerization of addition polymers on a commercial basis.

That the inclusion of antioxidants and antiozonates in polymers, including scrap tire rubber, has been and continues to be practiced to suppress the deleterious effect of ozone on polymers is well documented. The prior art, through domestic and foreign patents, also documents the treatment of whole tires or large chunks of scrap rubber by high temperature pyrolysis. The pyrolysis temperature, reported in both domestic and foreign patents and technical literature, is very high, commonly in the 650° C. to 800° C. temperature range. There have been, and continuing today, many technical investigations into recovering either energy or recyclable materials from scrap tire rubber in the United States and elsewhere. The results of a significant number of these have been published in the patent literature. Many different techniques are reported. Care must be taken in that a common definition of terminology was not used by all investigators. Essentially none of the past and present investigators have utilized the full benefits and catalyst chemistry to achieve more moderate operating conditions.

SUMMARY OF THE INVENTION

The principal objective of this invention is to simultaneously improve the process and its economics for the recovery of valuable hydrocarbons for reuse. Several improvements and objectives are involved in this principal objective.

One objective has been to simplify the process and improve the economics by eliminating a major feed preparation step from that described in the referenced issued patent and pending application.

A further objective has been to improve process economics and process control by changing the reaction pressure from a partial vacuum to a slight positive pressure by using balancing gas pressure of inert gas. This change has also simplified the design of the process reaction section and has eliminated the possibility of undesirable combustion reactions in the reaction mass.

A further objective is the recovery of unexpected valuable hydrocarbons in addition to those expected by thermodepolymerization.

Other objectives are accomplished by the prudent combination of thermocatalytic chemistry and reaction conditions to yield other valuable hydrocarbons at conditions, compositions, and yields beyond that predicted in published thermodynamic literature.

The inventor has learned that tire rubber contains a valuable oil added in concentrations of as high as 40 weight percent. The inventor is not aware of any previous investigator acknowledging the presence of this ingredient. It is a major objective of this invention to recover and recycle this valuable hydrocarbon.

The method of the present invention involves receipt of properly sized small particles of used tire rubber in the -6 mesh size range. The desired particle size of the particulate is dictated, in part, by the very poor thermal conductivity of rubber. Further, as the thermocatalytic reaction proceeds, the individual particles continuously diminish in size, exposing fresh surfaces for further reaction. Inasmuch as small particles enhance the thermocatalytic conversion, an economy is achieved by elimination of the step of removing the very fine particles from the feedstock. Also, while pretreatment with ozone gas does enhance the degradation reaction, the improvement which it contributes is not in keeping with the added equipment and operating costs associated with ozone gas treatment. Thus, a considerable improvement in process economics is effected by accepting a -6 mesh feedstock and eliminating the ozone gas pretreatment system.

Replacing the reactor vacuum system with a positive pressure sweep of inert gas effects a further improvement in process economics by simplifying the design of reactor hardware which, in turn, eliminates the possibility of air leaking into the reactor and, in turn, allowing combustion of some of the reaction products. This improvement replaces a costly vacuum system with a simple, low cost inert gas sparging system (see FIG. 4). The cost of the vacuum system is also eliminated. With this revision, the reactor is maintained under a positive inert gas pressure which is provided by a sparging of the reaction mass by a flow of inert gas up through the reaction mass and out via the product gas line, sweeping the products of the reaction with it before they can be chemically altered by the elevated temperatures in the reaction mass.

Two runs were conducted wherein a target temperature of 300° C. was exceeded due to poor control of the reaction temperature. In the first run the temperature averaged 333° C., while in the second run the reaction temperature averaged 306° C. In each case a considerable amount of product was collected in a liquid nitrogen trap. Both samples were analyzed by Saybolt Laboratories in Houston, Tex. Amazingly, no olefins were found. The individual species identified were paraffins and/or both straight chain and cyclic naphthenes, ranging from $C_3$ to $C_{10}$ in composition. The average molecular weight of the higher temperature run was lower than that for the lower temperature run. Further, the composite collection of products from each run were of sufficiently high octane value that the products as produced would be suitable for use as gasoline additives. In sum, the data clearly demonstrated that the temperature of the reaction has a profound effect on the chemical composition of the product, and illustrated that the process is versatile in that the type of product to be produced can be altered on demand or as market conditions dictate.

Upon termination of each run the reaction vessel was allowed to cool to room temperature before opening. In each case a considerable before amount of carbon black was poured from the reaction flask, and a crust of active catalyst and carbon black remained in the flask. Washing of the residue crust with water caused an immediate heating of the flask and crust showing that the catalyst was still active.

Regarding the depolymerization reaction, it is well-known that competing reactions occur in polymerization chemistry. The predominate reaction rate is a function of the temperature. The higher the temperature the greater the rate of decomposition or depolymerization reactions. Also, per Sawada, there is a ceiling temperature above which the depolymerization reaction predominates. The ceiling temperature is different for each monomer type. The ceiling temperatures of the monomers of interest are in the range from about 200° C. to about 550° C. Thus, the preferred reaction temperature is not a fixed temperature but is the temperature required for the specific polymers involved. Generally, the more complex the molecule or the higher its molecular weight, the higher its ceiling temperature.

Conditions do exist wherein the depolymerization reaction overwhelms the polymerization reaction. Generally, a combination of catalyst technologies are involved. The rubbers and polymers to be treated have been polymerized by a combination of catalysts, organo metallic halides, metallic oxides, free radical initiators and the like. Magnesium dichloride, or trimethyl aluminum (TEAL) are often involved as a cocatalyst. Referring to the Periodic Chart of the Elements, it is noted that the base metal in the majority of high activity addition polymerizations metallic salts are in classes III, IVB, and VIB having an electron structure that supports the acceptor/donor exchange requirement with the polymer undergoing decomposition or depolymerization. From the above, and other findings, it has been deduced that a molten $MgCl_2/AlCl_3$ catalyst combination will thermodynamically cause the thermocatalytic depolymerization degradation of polymers and rubbers in the temperature range described above. Other catalysts or catalyst systems which may be used include $BaCl_2/AlCl_3$; $LiAlCl_4$; $NaAlCl_4$; $KAlCl_4$; and other combinations of non-transition metal halides. The ratio of $MgCl_2$ to $AlCl_3$ is maintained to maximize the depolymerization of polymer or rubber to preferred hydrocarbons. Generally, this ratio will be in the range of 1:1 to about 2:1 on a molar basis. As the depolymerization reaction proceeds there will be a slow depletion of the $MgCl_2/AlCl_3$ catalyst on a ratio of about 1:50,000 of rubber processed. Make-up catalyst thus needs to be added to the reactor to sustain the reaction rate.

Recovery and separation of the hydrocarbons, carbon black and other hydrocarbons is a vital part of the economics of the process. Separation and recovery of hydrocarbons will use conventional techniques. The separation and recovery of the carbon black and other valuable hydrocarbons from the reactor residue can be via a series of solvent and water washes followed by specific purification procedures.

Examples of the more important features of this invention have been broadly outlined in order that the detailed description that follows may be better understood and so that the contributions which this invention provides to the art may be better appreciated. There are, of course, additional features of the invention which will be described herein and will be included within the subject matter of the claims appended hereto.

DETAILED DESCRIPTION OF A PREFERRED EMBODIMENT

Figure 1:
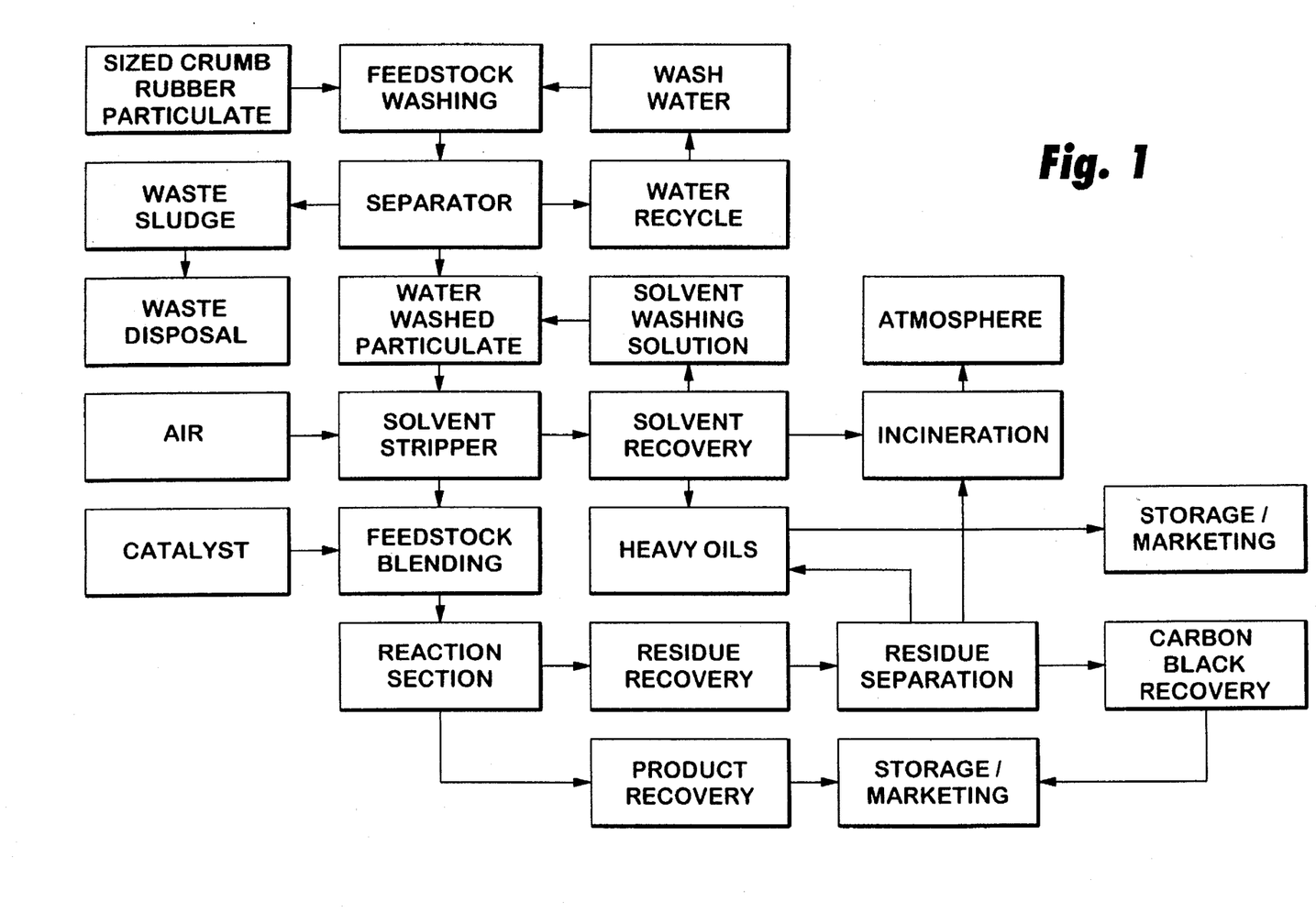
FIG. 1 is a block flow diagram of the process of this invention.

Additional objects, features, and advantages of the present invention will become apparent by referring to the following description of the invention in connection with the accompanying drawings. The basic processes for the degradation of used rubber and waste plastics are, for the most part, identical. Thermocatalytic conversion is a form of polymer degradation or decomposition. Thus, although waste plastics can be thermocatalytically converted according to the present invention, for simplicity reference in this section of the application is made only to the processing of used tire rubber. A block flow diagram for the process of this invention is shown as FIG. 1. As indicated herein, as a preliminary step to the depolymerization or thermocatalytic conversion, used tires will be collected, shredded to size, and steel wire and fabric will be removed from the rubber particles.

Feed Preparation Section

Figure 2:
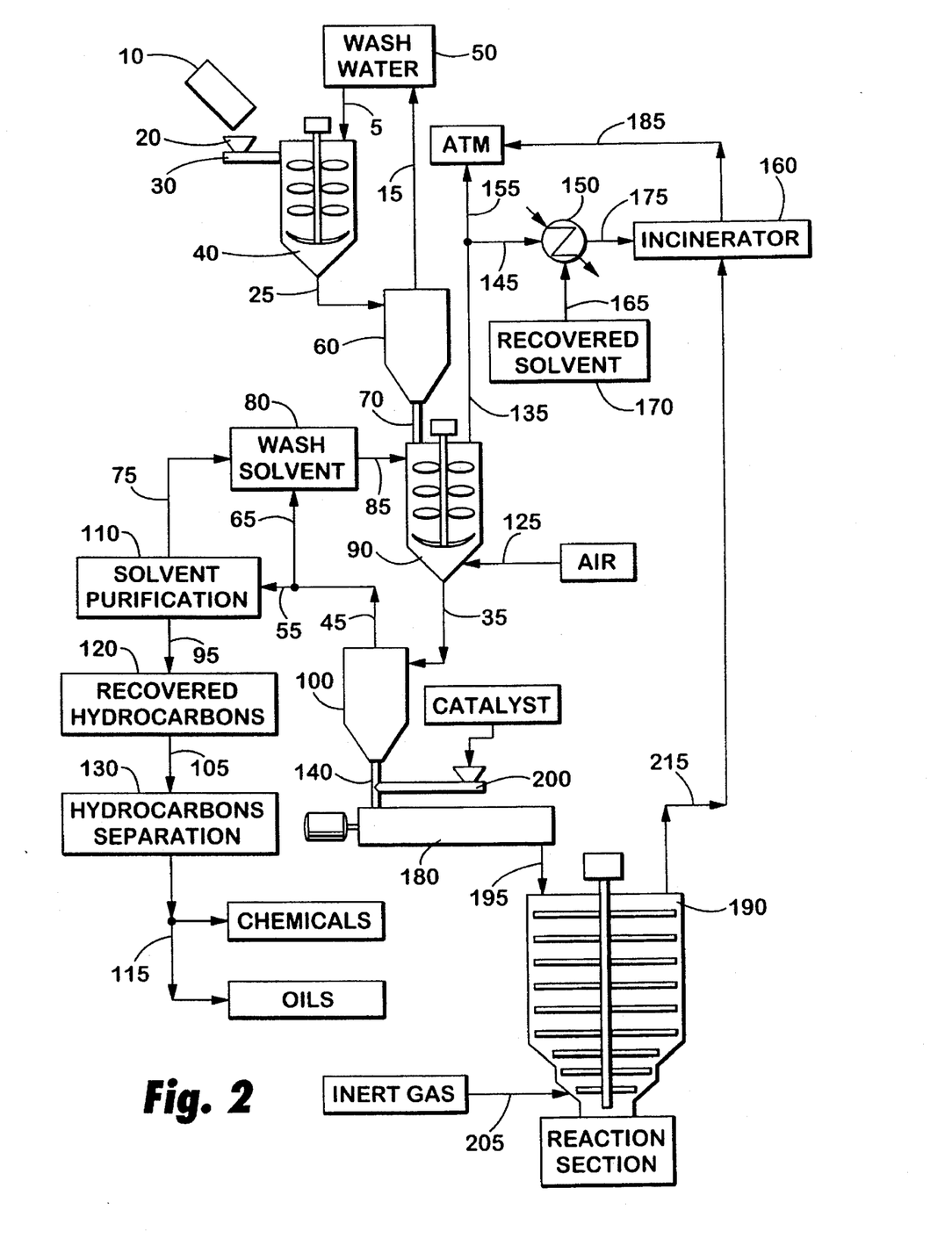
FIG. 2 is a schematic representation of the feed preparation section of this invention.

As illustrated in FIG. 2, small rubber particles of about -6 mesh are received from off-site sources via a hopper car or truck. Small rubber particles have a rather steep angle of repose, essentially eliminating gravity flow as a process condition. Thus, flow of the rubber particles is aided by steep angles, augers, or vibration. The hopper car will be inclined sufficiently that, with additional vibration, the rubber particles will flow from hopper car 10 through a hopper 20 and then be conveyed by auger 30 into the water wash hopper 40. It must be assumed that the small particles of rubber will be coated with dust and dirt which will be removed by washing in hopper 40. The wash hopper operates on a batch basis. A low speed stirrer agitates the batch during the washing to aid in removing the surface dirt and dust.

The rubber particles are flushed from the wash hopper 40 by the wash water through line 25 into hydroclone separator 60 where the washed rubber leaves as underflow from the hydroclone separator 60 through auger 70 into the batch solvent wash hopper 90. The wash water of the hydroclone overflow stream leaves through line 15 to the wash water feed tank 50 from which it can be reused via line 5 to the wash hopper 40. Auger 70 is used to insure positive transfer of the batch of rubber particles from hydroclone 60 to the solvent wash hopper 90.

With the start of the initial transfer of particulate to hopper 90, drying air is fed through line 125 into the bottom of hopper 90 and up through the bed of particulate which is agitated by a low speed mixer while the hopper is being filled. The moisture laden air existing hopper 90 will be vented to the atmosphere via line 155. The flow of drying air through the particulate is continued until a humidity gauge, not shown, mounted on line 135 indicates the batch of washed rubber has been sufficiently dried. This step is important because any traces of moisture will deactive the catalyst which is added later in the process. When the humidity gauge indicates the particulate has been dried the flush of drying air from line 125 is stopped and hopper 90 is filled with a washing solvent, which is one or a combination of simple organic hydrocarbon solvents such as tetrahydrofuran, methanol, or ethanol, being fed from solvent storage tank 80 via line 85. During the filling of hopper 90 with solvent and during the washing of the batch of rubber, the hopper contents are agitated by the low speed mixer. After a sufficient, prescribed period of agitated mixing and washing, the solvent and the particulate flow from hopper 90 via line 35 to a second hydroclone 100 where the overflow of solvent is returned through lines 45 and 65 to the wash solvent feed tank 80.

As the solvent is used in hydroclone 100 it absorbs antioxidant, antiozonate, and/or other stabilizing additives washed from the surface of the particulate. The contaminated solvent thus requires purification before being reused. This is accomplished by taking a constant percentage of flow in line 45 and diverting it through line 55 to the solvent purification system 110. The purified solvent is returned through line 75 to wash solvent tank 80 for reuse. The purification system will separate a concentrate of removed additives and convey them via line 95 to a mixed hydrocarbon recovery tank 120. The solution will be fed via line 105 to a separation facility 130 where valuable chemicals and oils will be recovered for resale.

Following the completion of the batch solvent washing step the inside surfaces of the batch solvent hopper 90 will be coated with a thin layer of solvent. It is necessary to remove this layer by air drying so the next batch can begin. Removal is necessary to avoid the discharge of hydrocarbon laden air to the atmosphere during the next batch operation. Otherwise, an additional vessel would need to be added for the air drying step. Thus, between batches the coated solvent wash hopper 90 is flushed with dry air via line 125, which is fed out the top of the hopper and via lines 135 and 145 through heat exchanger 150 to recover via line 165 the entrained wash solvent in tank 170, and to an incinerator 160 through line 175. The combustion products are vented to the atmosphere via line 185.

The underflow from hydroclone separator 100 is conveyed via a mechanically driven auger 140 to the ribbon blender 180. Catalyst, in the proper blended ratio, will be fed via weigh feeder 200 to auger 140 just above its discharge into ribbon blender 180. The amount of catalyst fed is the amount required to maintain the ratio of catalyst and rubber in the reactor 230 at a target concentration. Ribbon blender 180 feeds the particulate to the reaction section feed hopper 190. The catalyst is mixed with the rubber during that blending/conveying step. The ribbon blender discharge to the reaction section hopper 190 is via line 195. The feed preparation section, operating in a batch mode, preferably is sized to deliver sufficient feed to the reaction section feed hopper 190 so that it and all equipment downstream of it may operate continuously.

The reaction section feed hopper 190 is fitted with a combination mixer and vertical auger to avoid bridging of the rubber particles and to continuously feed particulate to the reaction section feed hoppers. During operation the internals of reaction section feed hopper 190 are continuously flushed with a flow of inert gas received via line 205. The flushing eliminates the possible influence of residual catalyst poisons in the system. Because they could contain hydrocarbons, the exiting flushing gases are fed via line 215 to the incinerator 160, with the combustion products being discharged to the atmosphere.

Thermocatalytic Reaction Section

Figure 3:
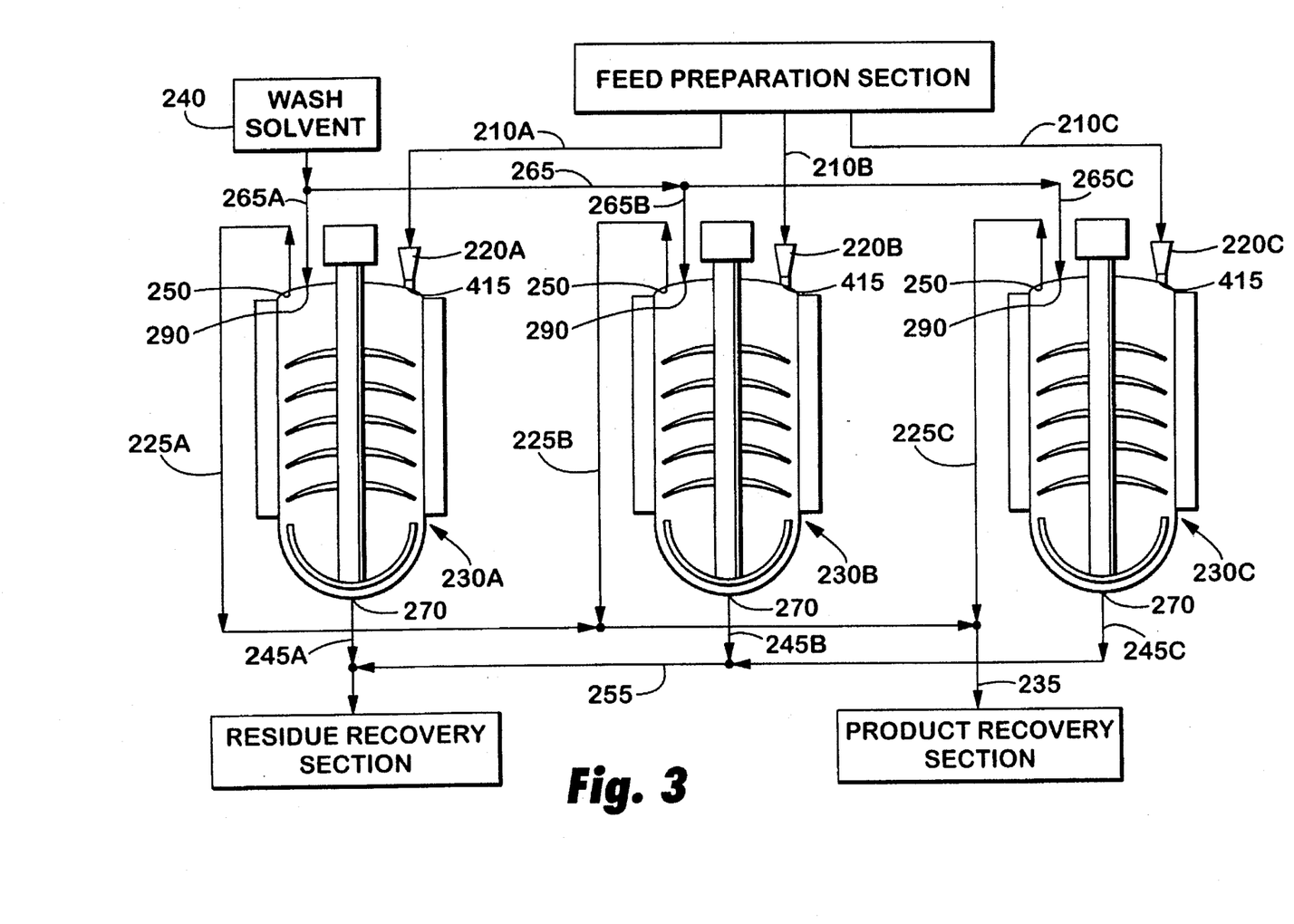
FIG. 3 is a schematic representation of the thermocatalytic reaction section of this invention.

Although the reaction section shown in FIG. 3 has three reactors which operate in parallel, the invention is not limited to such a combination or layout. Organization and plant layout preferably is based on a modular design concept where additional reactors may be added or removed as required. The multiple reactor concept accommodates an operating concept that single reactors may be taken off line for maintenance or other purposes without seriously restricting the overall plant operation.

Washed rubber feedstock is continuously conveyed from reaction section feed hopper 190 to thermocatalytic reactors 230A, 230B, and 230C through individual weigh conveyors 210A, 210B, and 210C. The feed to the reactors preferably is continuous and constant. The feed rate is maintained at a rate through reactor feed hoppers 220A, 220B, and 220C which will maintain a substantially constant reaction mass temperature in the thermocatalytic reactors 230A, 230B, 230C. As fresh blended feedstock of rubber and catalyst are added, heat input is required to maintain the reaction temperature at the desired level. This is accomplished via a hot oil heating system preferably comprising a hot oil jacket 405 that responds to the heat requirements via a thermocouple inserted through thermocouple part 400 into well 260, controlling the temperature of the oil circulated through the reactor jacket 405 of the reactor.

Figure 4:
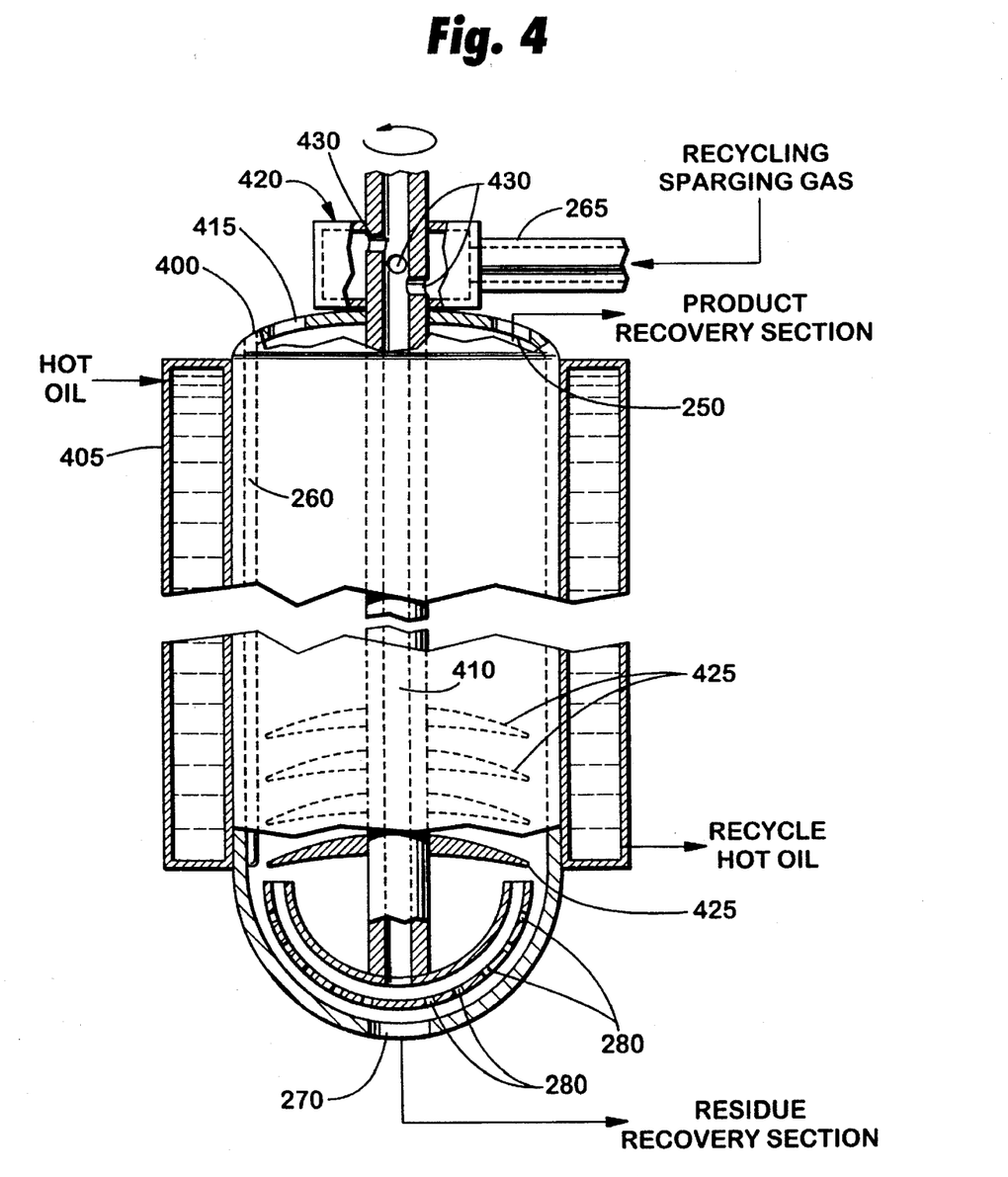
FIG. 4 is an expanded schematic representation of the reactor vessel.
Figure 5:
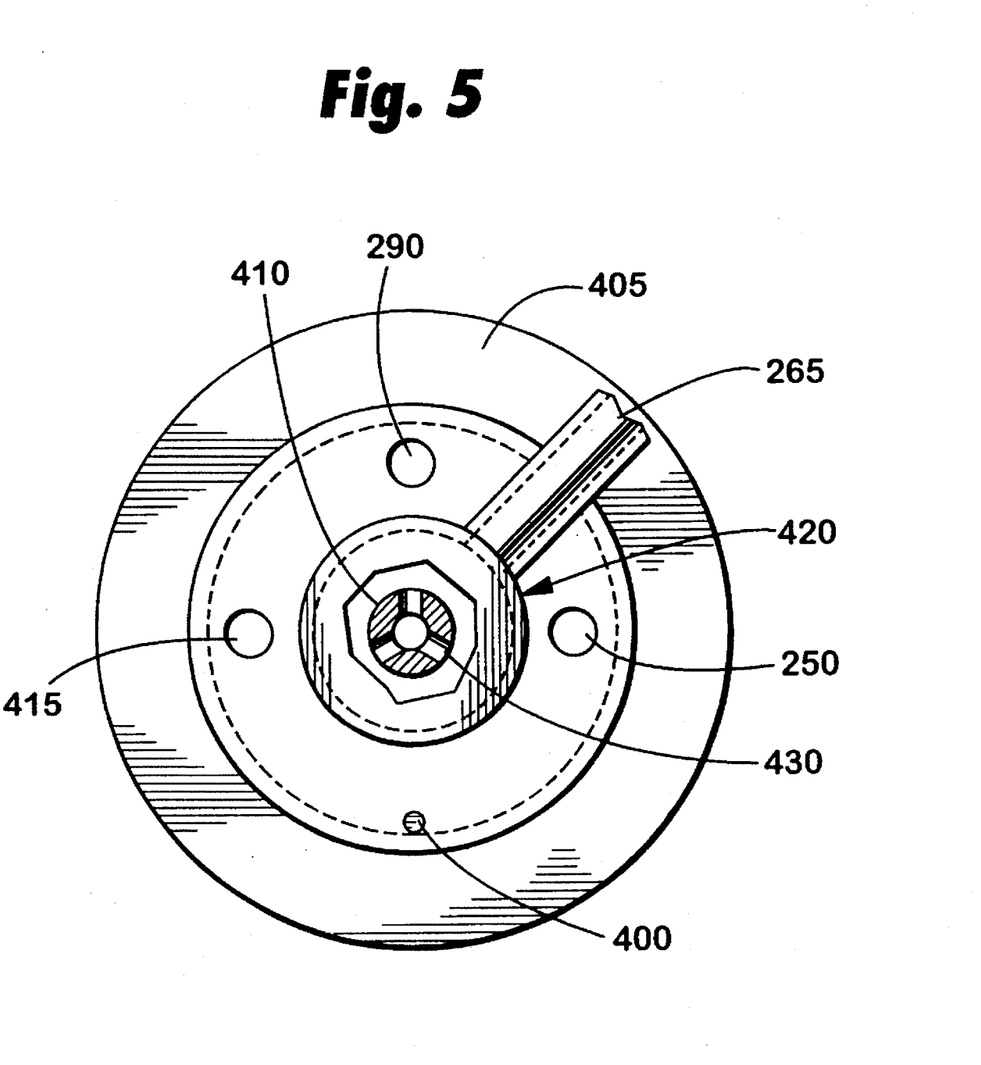
FIG. 5 is a top view of the reactor vessel of FIG. 4 showing the orientation of the various ports.

Each of the thermocatalytic reactors is equipped with a low speed mixer to continuously agitate the reaction mass so that, as much as possible, a uniform temperature is maintained in the reaction mass. The anchor stirrer and the essentially horizontal stirrer blades 425 sweep the reactor volume close to the inner reactor wall to maximize good heat transfer from the hot oil system and to maximize the maintenance of a uniform temperature throughout the reaction mass. Preferably, the temperature within the reactor is held substantially constant, i.e. it does not vary much more than about plus or minus 10° C. from about the reactor target temperature selected for the production of the desired product. Preferably, the prescribed or target temperature is between about 200° C. and about 400° C.

The reactors 230A, 230B, 230C are maintained at a slight positive pressure by the flow of inert sparger gas down the center of the hollow stirrer shaft 410 and out through sparger ports 280 located on the lower side of the hollow anchor stirrer blade. Preferably, the pressure within the reactor is maintained between about 1.1 and about 1.5 atmospheres absolute. The inert sparger gas passes upward through the reaction mass and out of the product off gas port 250, commingling with the product gases and sweeping them to the downstream product recovery system. The inert sparger gas is recovered in the product recovery system and recycled back to the thermocatalytic reactors via line 265 where they reenter the sparger gas feed assembly 420, enter the hollow stirrer shaft through the sparger gas perforations 430 and repeat the sparging process again. The recycled sparger gases may bring with them a small concentration of product gases, such as hydrogen, which will be recirculated without incident. FIG. 4 illustrates the flow pattern.

The thermocatalytic or conversion reaction proceeds rapidly. The catalyst maintains its activity for an extended period of time. The lower the ratio of catalyst to polymer, the longer the residence time in the reactor and the slower the reaction rate. However, the target concentration or ratio of catalyst to polymer will depend on what the process economics will tolerate for a given application. Preferably, though, the weight ratio will be between about 2.5 and 7.5 percent. As the thermocatalytic reaction proceeds, the gaseous products formed exit the reactor via port 250 and travel via lines 225A, 225B, and 225C to line 235 which conveys them to the product recovery section where a series of condensers/traps separately condense the product gases and collect them according to initial boiling point. A final cold trap condenses and collects all other low molecular weight products for future reference. As a point of concern, the length of the lines to the product recovery section should be relatively short to minimize the effect of ambient conditions.

Periodically, each of the thermocatalytic reactors must release a discharge of the reactor contents to the reactor residue recovery section via reactor discharge port 270 and lines 245A, 245B, 245C, and 255. This discharge is necessary to maintain continuous operation of the reactor, and will contain a mixture of (1) unreacted rubber; (2) carbon black; and (3) active catalyst. The separation and recovery of valuable products from the discharge may be done out-of-line. Also, periodically the internals the thermocatalytic reactors are washed to remove any build-up that may have accumulated on the stirrer and/or the inner reactor walls. Prior to this reactor washing, the feed of particulate and catalyst is stopped, and reaction activity is allowed to die. Flow of the sparger gas is stopped and the product off gas line is closed. Operation of the stirrer and reactor temperature may be maintained. Wash solvent, such as tetrahydrofuran or ethanol, is fed from wash solvent tank 240 to the top of the reactor being washed via line 265 and introduced through port 290 into the reactor under treatment. A spray nozzle mounted inside each reactor under port 290 distributes solvent throughout the interior of the reactor under treatment. The solvent spray flushes the surfaces of the stirrer and the internal reactor walls. The hot solvent wash is continued for several minutes, and wash solvent and the residue removed is dumped to the residue recovery section where the catalyst, being soluble in methanol, is separated from the solvent and carbon black and considered for reuse. Recovery of the carbon black for resale requires a series of drying and regeneration steps which, as stated above, are accomplished out-of-line.

Although the preferred embodiment of this invention has been described hereinabove in some detail, it should be appreciated that a variety of embodiments will be readily available to persons utilizing such for a specific end use. The description of the method of this invention is not intended to be limiting on this invention, but is merely illustrative of the preferred embodiment of this invention. Other methods of resource recovery which incorporate modifications or charges to that which has been described herein are equally included within this application.

What is claimed is:

1. A process for the recovery of gaseous hydrocarbons from addition polymer feedstock comprising:
   (a) washing the addition polymer feedstock to remove stabilizing additives from the surface of the feedstock;
   (b) blending the washed addition polymer feedstock with a catalyst to form a mixture, wherein said catalyst is a combination of magnesium dichloride and aluminum trichloride;
   (c) feeding the mixture into a heated reactor;
   (d) maintaining the mixture within the reactor at a prescribed temperature for a time sufficient to convert the washed addition polymer feedstock to gaseous hydrocarbons; and
   (e) removing the gaseous hydrocarbons from the reactor.

2. The process of claim 1 wherein a simple organic hydrocarbon solvent is used to remove the stabilizing additives from the surface of the feedstock.

3. The process of claim 1 wherein the addition polymer feedstock comprises rubber particles of -6 mesh size.

4. The process of claim 1 wherein the prescribed temperature is between about 200° C. and about 400° C.

5. The process of claim 1 wherein the prescribed temperature is held substantially constant about a target temperature.

6. The process of claim 1 wherein the catalyst is a mixture of magnesium dichloride and aluminum chloride in a molar ratio of between about 1:1 and about 2:1.

7. The process of claim 1 wherein the weight ratio of the catalyst to washed addition polymer feedstock is between about 2.5 and about 7.5 percent.

8. The process of claim 1 wherein the pressure within the reactor is maintained between about 1.1 and about 1.5 atmospheres absolute.

9. The process of claim 8 wherein the pressure within the reactor is maintained by an inert gas.

10. The process of claim 9 wherein the inert gas is introduced as a sparger gas near the bottom of the reactor and sweeps the gaseous hydrocarbons from the reactor.

11. The process of claim 1 wherein the gaseous hydrocarbons are olefins.

12. The process of claim 1 wherein the gaseous hydrocarbons are paraffins.

13. The process of claim 1 wherein the gaseous hydrocarbons are naphthenes.

14. The process of claim 1 wherein the gaseous hydrocarbons have an aliphatic or cyclic molecular structure.

15. The process of claim 1 wherein the addition polymer feedstock is rubber reclaimed from used tires.

16. The process of claim 1 wherein the addition polymer feedstock is of polyolefin origin.

17. The process of claim 1 wherein the addition polymer feedstock is a blend of homopolymer and copolymer feedstocks of polyolefin origin.

\* \* \* \* \*